United States Patent [19]

DeLuca et al.

[11] Patent Number: 5,373,004
[45] Date of Patent: Dec. 13, 1994

[54] 26,28-METHYLENE-1α, 25-DIHYDROXYVITAMIN $D_2$ COMPOUNDS

[75] Inventors: Hector F. DeLuca, Deerfield, Wis.; Naoshi Nakagawa, Kurashiki, Japan

[73] Assignee: Wisconsin Alumni Research Foundation, Madison, Wis.

[21] Appl. No.: 157,970

[22] Filed: Nov. 24, 1993

[51] Int. Cl.⁵ ............................................. C07C 401/00
[52] U.S. Cl. ..................................... 514/167; 550/653
[58] Field of Search .......................... 514/167; 552/653

[56] References Cited

U.S. PATENT DOCUMENTS

| | | | |
|---|---|---|---|
| 4,511,564 | 4/1985 | Ishizuka et al. | 514/167 |
| 4,512,925 | 4/1985 | DeLuca et al. | 514/167 |
| 4,588,716 | 5/1986 | DeLuca et al. | 514/168 |
| 4,769,181 | 9/1986 | DeLuca et al. | 260/397.2 |
| 4,851,401 | 7/1989 | DeLuca et al. | 514/167 |
| 4,866,048 | 9/1989 | Calverley et al. | 514/167 |
| 4,973,584 | 11/1990 | DeLuca et al. | 514/167 |
| 5,190,935 | 3/1993 | Binderup et al. | 514/167 |
| 5,194,431 | 3/1993 | DeLuca et al. | 514/167 |
| 5,206,229 | 4/1993 | Calverley et al. | 514/167 |
| 5,250,523 | 10/1993 | DeLuca et al. | 514/167 |

FOREIGN PATENT DOCUMENTS

WO89/10351  11/1989  WIPO .

Primary Examiner—Johann Richter
Assistant Examiner—Kimberly J. Kestler
Attorney, Agent, or Firm—Andrus, Sceales, Starke & Sawall

[57] ABSTRACT

Vitamin $D_2$ analogs in which a cyclopentane ring is introduced into the side chain of 1α,25-dihydroxyvitamin $D_2$. The compounds are characterized by a marked intestinal calcium transport activity while exhibiting much lower activity than 1α,25-dihydroxyvitamin $D_3$ in their ability to mobilize calcium from bone. Because of their preferential calcemic activity, these compounds would be useful for the treatment of diseases where bone formation is desired, such as osteoporosis.

18 Claims, No Drawings

26,28-METHYLENE-1α, 25-DIHYDROXYVITAMIN D$_2$ COMPOUNDS

This invention was made with United States Government support awarded by the National Institutes of Health (NIH), Grant No. DK-14881. The United States Government has certain rights in this invention.

BACKGROUND OF THE INVENTION

This invention relates to biologically active vitamin D compounds. More specifically, the invention relates to 26,28-Methylene-1α,25-dihydroxyvitamin D$_2$ compounds, to a general process for their preparation, and to their use in treating osteoporosis.

With the discovery of 1α,25-dihydroxyvitamin D$_3$ as the active form of the vitamin has come an intense investigation of analogs of this hormonal form of vitamin D with the intent of finding analogs that have selective activity. By now, several compounds have been discovered which carry out the differentiative role of 1,25-dihydroxyvitamin D$_3$ while having little or no calcium activity. Additionally, other compounds have been found that have minimal activities in the mobilization of calcium from bone while having significant activities in stimulating intestinal calcium transport. Modification of the vitamin D side chain by lengthening it at the 24-carbon has resulted in loss of calcium activity and either an enhancement or undisturbed differentiative activity. Placing the 24-methyl of 1α,25-dihydroxyvitamin D$_2$ in the epi-configuration appears to diminish activity in the mobilization of calcium from bone. On the other hand, increased hydrophobicity on the 26- and 27-carbons seems to increase the total activity of the vitamin D compounds provided the 25-hydroxyl is present.

Several of these known compounds exhibit highly potent activity in vivo or in vitro, and possess advantageous activity profiles. Thus, they are in use, or have been proposed for use, in the treatment of a variety of diseases such as renal osteodystrophy, vitamin D-resistant rickets, osteoporosis, psoriasis, and certain malignancies.

It is well known that females at the time of menopause suffer a marked loss of bone mass giving rise ultimately to osteopenia, which in turn gives rise to spontaneous crush fractures of the vertebrae and fractures of the long bones. This disease is generally known as postmenopausal osteoporosis and presents a major medical problem, both in the United States and most other countries where the life-span of females reaches ages of at least 60 and 70 years. Generally, the disease which is often accompanied by bone pain and decreased physical activity, is diagnosed by one or two vertebral crush fractures with evidence of diminished bone mass. It is known that this disease is accompanied by diminished ability to absorb calcium, decreased levels of sex hormones, especially estroen and androgen, and a negative calcium balance.

Similar symptoms of bone loss characterize senile osteoporosis and steroid-induced osteoporosis, the latter being a recognized result of long term glucocorticoid (cortico-steroid) therapy for certain disease states.

Methods for treating the disease have varied considerably but to date no totally satisfactory treatment is yet known. A conventional treatment is to administer a calcium supplement to the patient. However, calcium supplementation by itself has not been successful in preventing or curing the disease. Another conventional treatment is the injection of sex hormones, especially estrogen, which has been reported to be effective in preventing the rapid loss of bone mass experienced in postmenopausal women. This technique, however, has been complicated by the fact of its possible carcinogenicity. Other treatments for which variable results have been reported, have included a combination of vitamin D in large doses, calcium and fluoride. The primary problem with this approach is that fluoride induces structurally unsound bone, called woven bone, and in addition, produces a number of side effects such as increased incidence of fractures and gastrointestinal reaction to the large amounts of fluoride administered. Another suggested method is to block bone resorption by injecting calcitonin or providing phosphonates.

U.S. Pat. No. 4,225,596 suggests the use of various metabolites of vitamin D$_3$ for increasing calcium absorption and retention within the body of mammals displaying evidence of or having a physiological tendency toward loss of bone mass. The metabolites specifically named in that patent, i.e., 1α-hydroxyvitamin D$_3$, 1α-hydroxyvitamin D$_2$, 1α,25-dihydroxyvitamin D$_3$, 1α,25-dihydroxyvitamin D$_2$ and 1,24,25-trihydroxyvitamin D$_3$, although capable of the activity described and claimed in that patent are also characterized by the disadvantage of causing hypercalcemia especially if used with the conventional calcium supplement treatment. Therefore, use of these compounds to treat osteoporosis has not been widely accepted. U.S. Pat. Nos. 3,833,622 and 3,901,928 respectively suggest using the hydrate of 25-hydroxyvitamin D$_3$ and 1α-hydroxyvitamin D$_3$ for treatment of osteoporosis in a general expression of utility for those compounds. It is well known both of those compounds express traditional vitamin D-like activity, including the danger of hypercalcemia.

U.S. Pat. No. 4,588,716 also suggests the use of 1α,25-dihydroxy-24-epi-vitamin D$_2$ to treat bone disorders characterized by the loss of bone mass, such as osteoporosis. This compound expresses some of the vitamin D-like characteristics affecting calcium metabolism such as increasing intestinal calcium transport and stimulating the mineralization of new bone, but has the advantage of minimal effectiveness in mobilizing calcium from bone. The 24-epi compound may be administered alone or in combination with a bone mobilization-inducing compound such as a hormone or vitamin D compound such as 1α-hydroxyvitamin D$_3$ or D$_2$ or 1α,25-dihydroxyvitamin D$_3$ or D$_2$.

U.S. Pat. No. 5,194,431 discloses the use of 24-cyclopropane vitamin D$_2$ compounds in treating osteoporosis. Also, U.S. Pat. No. 4,851,401 discloses the use of cyclopentano-1,25-dihydroxyvitamin D$_3$ compounds in the treatment of osteoporosis and related diseases.

SUMMARY OF THE INVENTION

The present invention provides novel compounds exhibiting a desired, and highly advantageous, pattern of biological activity. These compounds are characterized by a marked intestinal calcium transport activity, as compared to that of 1α,25-dihydroxyvitamin D$_3$, while exhibiting much lower activity than 1α,25-dihydroxyvitamin D$_3$ in their ability to mobilize calcium from bone. Hence, these compounds are highly specific in their calcemic activity. Their preferential activity on intestinal calcium transport and reduced calcium mobilizing activity in bone allows the in vivo administration of these compounds for the treatment of metabolic bone diseases where bone loss is a major concern. Because of their preferential calcemic activity, these compounds would be preferred therapeutic agents for the treatment of diseases where bone formation is desired, such as osteoporosis, osteomalacia and renal osteodystrophy.

Structurally, the key feature of the compounds having these desirable biological attributes is that they are analogs of 1,25-dihydroxyvitamin $D_2$ in which a cyclopentane ring is introduced onto the side chain. Thus, the compounds of this type are characterized by the following general structure:

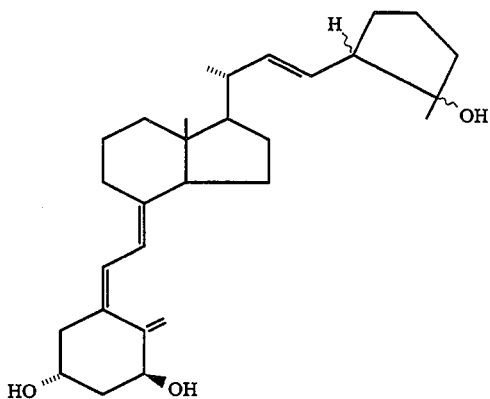

The present invention, therefore, provides novel compounds showing preferential activity on intestinal calcium transport and reduced calcium mobilizing activity in bone, or high bone calcium mobilizing activity. The reduced bone mobilizing activity would make these compounds especially suitable to treat osteoporosis where bone turnover is high (i.e. postmenopausal type), while the compounds having high bone calcium mobilizing activity would be suitable for low turnover osteoporosis such as age-related osteoporosis. More specifically, the compounds are (22E, 24R, 25R)-26,28-methylene-1α,25-dihydroxyvitamin $D_2$; (22E, 24S, 25S)-26,28-methylene-1α,25-dihydroxyvitamin $D_2$; (22E, 24R, 25S)-26,28-methylene-1α,25-dihydroxyvitamin $D_2$; and (22E, 24S, 25R)-26,28-methylene-1α,25-dihydroxyvitamin $D_2$.

This invention also provides novel intermediate compounds formed during the synthesis of the end products. Structurally, the intermediate compounds are characterized by the following general structure:

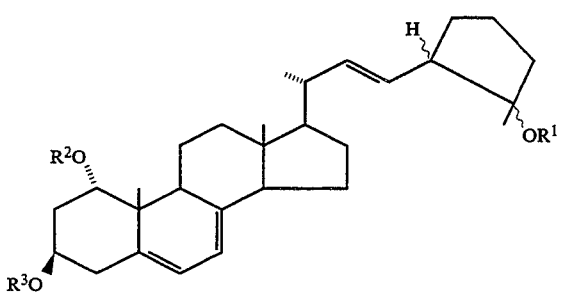

where R1, R2 and R3 may be hydrogen or a hydroxy-protecting group.

In another aspect of the invention, it has now been found that the loss of bone mass, which is characteristic of osteoporosis may be effectively treated by the administration of a 26,28-methylene-1α,25-dihydroxyvitamin $D_2$ compound in sufficient amounts to increase bone mass. More specifically, a method of treating osteoporosis comprises the administration of an effective amount of any of the above four isomers of 26,28-methylene-1α,25-dihydroxyvitamin $D_2$. The above compounds may be administered alone or in combination with other pharmaceutically acceptable agents. Dosages of from not less than about 0.5 μg/day to not more than about 50 μg/day of the individual compound per se, or in combinations, are generally effective. This method has the distinct advantage that it will restore bone mass due to the insignificant bone mobilization activity of this compound and further this compound advantageously will not cause hypercalcemia even if the compound is administered continuously on a daily basis, as long as the appropriate compound dosages are used, it being understood that the dosage levels will be adjusted dependent on the response of the subject as monitored by methods known to those skilled in the art.

The above method, involving the administration of the indicated dosages of any one of the four isomers of 26,28-methylene-1α,25-dihydroxyvitamin $D_2$ is effective in restoring or maintaining bone mass, and thus provides a novel method for the treatment or prevention of various forms of osteoporosis such as postmenopausal osteoporosis, senile osteoporosis and steroid-induced osteoporosis. It will be evident that the method will also find ready application for the prevention or treatment of disease states other than those named, in which the loss of bone mass is an indication.

DETAILED DESCRIPTION OF THE INVENTION

As used in the description and in the claims, the term hydroxy-protecting group signifies any group commonly used for the temporary protection of hydroxy functions, such as for example, alkoxycarbonyl, acyl, alkylsilyl, alkylarylsilyl, and alkoxyalkyl groups, and a protected hydroxy group is a hydroxy function derivatized by such a protecting group. Alkoxycarbonyl protecting groups are groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term 'acyl' signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word 'alkyl' as used in the description or the claims, denotes a straight-chain or branched hydrocarbon radical of 1 to 10 carbons, in all its isomeric forms. Alkoxyalkyl protecting groups are groupings such as methoxymethyl, ethoxyethyl, methoxyethoxymethyl, or tetrahydrofuranyl and tetrahydropyranyl. Preferred alkylsilyl-protecting groups are trimethylsilyl, triethylsilyl, t-butyldimethylsilyl, and analogous alkylated silyl radicals. Alkylarylsilyl protecting groups are groupings such as tert-butyldiphenylsilyl.

The vitamin D compounds useful in the present treatment are (22E, 24R, 25R)-26,28-methylene-1α,25-dihydroxyvitamin $D_2$; (22E, 24S, 25S)-26,28-methylene-1α,25-dihydroxyvitamin $D_2$; (22E, 24R, 25S)-26,28-methylene-1α,25-dihydroxyvitamin $D_2$; and (22E, 24S, 25R)-26,28-methylene-1α,25-dihydroxy-vitamin $D_2$. The above compounds may be administered alone or in combination with other pharmaceutically acceptable agents.

The vitamin D compounds or combinations thereof can be readily administered as sterile parenteral solutions by injection or intravenously, or by alimentary canal in the form of oral dosages, or trans-dermally, or by suppository. Doses of from about 0.5 micrograms to about 50 micrograms per day of the 26,28-methylene-1α-hydroxyvitamin $D_2$ compounds per se, or in combination with other 1α-hydroxylated vitamin D compounds, the proportions of each of the compounds in the combination being dependent upon the particular disease state being addressed and the degree of bone mineralization and/or bone mobilization desired, are generally effective to practice the present invention. In all cases sufficient amounts of the compound should be used to restore bone mass. Amounts in excess of about 50 micrograms per day or the combination of that compound with other 1α-hydroxylated vitamin D compounds, are generally unnecessary to achieve the desired results, may result in hypercalcemia, and may not be am economically sound practice. In practice the higher doses are used where therapeutic treatment of a disease state is the desired end while the lower doses are generally used for prophylactic purposes, it being understood that the specific dosage administered in any given case will be adjusted in accordance with the specific compounds being administered, the disease to be treated, the condition of the subject and the other relevant medical facts that may modify the activity of the drug or the response of the subject, as is well known by those skilled in the art. For example, to be effective, the 26,28-methylene-1α,25-dihydroxyvitamin $D_2$ compounds are preferably administered in a dosage range of 0.5-50 μg/day. In general, either a single daily dose or divided daily dosages may be employed, as is well known in the art.

Dosage forms of the various compounds can be prepared by combining them with non-toxic pharmaceutically acceptable carriers to make either immediate release or slow release formulations, as is well known in the art. Such carriers may b either solid or liquid such as, for example, corn starch, lactose, sucrose, peanut oil, olive oil, sesame oil and propylene glycol. If a solid carrier is used the dosage form of the compounds may be tablets, capsules, powders, troches or lozenges. If a liquid carrier is used, soft gelatin capsules, or syrup or liquid suspensions, emulsions or solutions may be the dosage form. The dosage forms may also contain adjuvants, such as preserving, stabilizing, wetting or emulsifying agents, solution promoters, etc. They may also contain other therapeutically valuable substances.

The present invention is more specifically described by the following examples, which are meant to be illustrative only of the process of synthesis and of the novel compounds, both end products and intermediates, obtainable thereby. In these examples, specific compounds identified by Arabic numerals (e.g. compounds 1, 2, 3, . . . etc.) refer to the structures so numbered in the process schematics. Additionally examples are provided which are illustrative of the distinctive biological characteristics of the new compounds, such characteristics serving as a basis for the application of these compounds in the treatment of metabolic bone disease.

Preparation of Compounds

General Procedures. Ultraviolet (UV) absorption spectra were recorded on a Shimadzu UV-Visible recording spectrophotometer. Proton nuclear magnetic resonance ($^1$H-NMR) spectra were recorded on a Bruker AM-500 multinuclear spectrometer at 500 MHz or on a JEOL JNM-GSX 270 FT NMR spectrometer at 270 MHz in chloroform-d ($CDCl_3$). Chemical shifts (δ) are reported downfield from internal tetramethylsilane (TMS: δ0.00). Mass spectra (MS) were recorded at 70eV on a JEOL JMS-HX100 mass spectrometer equipped with a JEOL JMA-DA5000 mass data system. Silica gel 60 (Merck, 230–400 mesh) was used for column chromatography. High performance liquid chromatography (HPLC) was performed using a Waters Associates Liquid chromatography equipped with a Model 6000A solvent delivery system, a Model U6K injector and a Model 450 variable wavelength detector or using a Shimadzu L-6AD liquid chromatograph system equipped with a Rheodyne 7125 injector, a Shimadzu SPD-6A UV spectrophotometric detector, a Shimadzu FCV-100B fraction collector and a Shimadzu C-R4A chromatopac. Tetrahydrofuran was distilled from sodium-benzophenone ketyl under nitrogen. Other solvents were purified by standard method.

In the Process Scheme the following abbreviations are employed:
Et: ethyl
Ts: toluenesulfonyl
Ph: phenyl
Bn: benzyl
Bu: butyl
THF: tetrahydrofuran
Me: methyl
DMAP: 4-dimethylaminopyridine
DMF: N,N-dimethylformamide
mCPBA: 3-chloroperbenzoic acid
TES: triethylsilyl
Tf: trifluoromethanesulfonyl It should be noted that in the present description and in the Scheme, compound 12 is a known compound and may be prepared in accordance with PCT Patent Application No. WO88/07545.

EXAMPLE 1

Synthesis of Four Isomers of 26,28-Methylene-1α,25-dihydroxyvitamin $D_2$ (compounds 15a, 15a', 15b and 15b'; Process Scheme).

The synthesis of compounds 15a, 15a', 15b and 15b' may be summarized as follows:

The starting material was commercially available ethyl 2-oxocyclopentanecarboxylate 1. The ketone group was protected as an acetal (compound 2) and the ester was reduced with lithium aluminum hydride to yield alcohol 3. The hydroxyl group of 3 was protected as a benzyl ether (compound 4) and the ketone functionality was regenerated by treatment with an acid catalyst in acetone to provide ketone 5. On treatment with methylmagnesium bromide were obtained the diastereomeric alcohols 6a and 6b, which were able to be separated by chromatography, and thereafter the two diastereomers were converted separately.

The benzyl protective group of 6a was removed under hydrogenation condition to give diol 7a. The primary hydroxyl group of diol 7a was converted into the corresponding tosylate (compound 8a), and the tosyloxy group was substituted with phenylthio group on treatment with thiophenoxide to yield phenylsulfide 9a. The phenylsulfide was oxidized with a peracid to the corresponding phenylsulfone (compound 10a), and finally the protection of the hydroxyl group as a silyl ether to give the side chain sulfone 11a. In the same manner, the diastereomer 6b was converted into the sulfone 11b.

Julia olefination methodology was used for coupling with a steroidal aldehyde 12 and formation of the trans double bond. Thus, the anion of the sulfones 11a or 11b was condensed with aldehyde 12, and the resulting hydroxy sulfone was submitted to reductive elimination reaction with sodium amalgam, after treated with acetic anhydride, to give compound 13a or 13b, respectively. Deprotection of the silyl protective groups with fluoride ion provided the provitamins 14a and 14b, which were converted into mixtures of vitamin D derivatives 15a and 15a', or 15b and 15b', respectively, in a usual manner (photo- and thermoisomerization, followed by deprotection). HPLC purification and separation gave four possible isomers 15a, 15a', 15b and 15b', derived from the chiral centers of carbon-24 and carbon-25.

6-Ethoxycarbonyl-1,4-dioxaspiro[4.4]nonane 2.

A mixture of ethyl 2-oxocyclopentanecarboxylate (Aldrich, 10.0 g, 64.0 mmol), ethylene glycol (18 mL, 323 mmol), triethyl orthoformate (21 mL, 126 mmol) and p-toluenesulfonic acid monohydrate (0.61 g, 3.21 mmol) in toluene (150 mL) was heated under reflux with removing distillate with a Dean-Stark apparatus for 1 h. The mixture was cooled and poured into NaHCO3 solution, and the organic layer was separated. The aqueous layer was extracted with diethyl ether, and the combined organic layers were washed with NaCl solution and dried over Na2SO4. Filtration and concentration gave 16.41 g of 2, as a pale yellow oil, which was used in the next reaction without further purification.

$^1$H-NMR δ(ppm, 500 MHz): 1.27 (3H, t, J=7.3 Hz), 1.58–1.73 (1H, m), 1.77–1.88 (2H, m), 1.88–1.98 (2H, m), 2.07–2.17 (1H, m), 2.90 (1H, t, J=8.0 Hz), 3.86–3.98 (3H), 3.98–4.06 (1H, m), 4.09–4.23 (2H, m)

6-Hydroxymethyl-1,4-dioxaspiro[4.4]nonane 3.

To a suspension of lithium aluminum hydride (2.43 g, 64.0 mmol) in diethyl ether (50 mL) was added a solution of 2 (16.41 g, crude) dropwise under nitrogen in an ice batch over a period of 50 min. To the mixture was added lithium aluminum hydride (1.2 g) and the mixture was stirred for 25 min. To the mixture were added water (3.6 mL), 15% NaOH solution (10.8 mL), water (10.8 mL) and Na2SO4 (20 g). The mixture was filtered through a pad of Celite and washed thoroughly with EtOAc. The filtrate and washings were combined and concentrated to give 10.95 g of 3, as a pale yellow oil, which was used in the next reaction without further purification. 15 $^1$H-NMR δ(ppm, 500 MHz): 1.49–1.96 (6H), 2.14 (1 H, m), 2.65 (1H, br s), 3.57–3.75 (2H), 3.85–4.08 (4H).

6-Benzyloxymethyl-1,4-dioxaspiro[4.4]nonane 4.

To a suspension of sodium hydride (60% dispersion, 2.82 g, 70.5 mmol) in THF (30 mL) was added a solution of 3 (10.95 g, crude) in THF (50 mL) dropwise in an ice bath over a period of 30 min. To the mixture was added tetra-n-butylammonium iodide (2.36 g, 6.39 mmol), followed by benzyl chloride (9 mL, 78.2 mmol), and the mixture was stirred at ambient temperature overnight. The mixture was heated under reflux for 50 min. The mixture was cooled and poured into ice water, and the organic layer was separated. The aqueous layer was extracted with diethyl ether, and the combined organic layers were washed with CaCl solution, and dried over Na2SO4. Filtration and concentration gave 21.02 g of an oily material, which was purified by column chromatography (SiO2 gel 100 g, EtOAc in n-hexane 0–10%), to give 12.94 g (81.4% from 1) of 4, as a pale yellow oil.

$^1$H-NMR δ(ppm, 500 MHz): 1.42–1.56 (1H, m), 1.56–1.87 (4H), 1.97 (1H, m), 2.29 (1H, m), 3.37 (1H, dd, J=9.4 and 7.6 Hz), 3.59 (1H, dd, J=9.4 and 6.2 Hz), 3.79 –4.01 (4H), 4.50 (1H, d, J=12.0 Hz), 4.52 (1H, d, J=12.0 Hz), 7.24 –7.43 (5H).

2-Benzyloxymethylcyclopentan-1-one 5.

A mixture of 4 (7.95 g, 32.0 mmol) and p-toluenesulfonic acid monohydrate (0.30 g, 1.58 mmol) in acetone (160 mL) was stirred at ambient temperature for 100 min. The mixture was neutralized with NaHCO3 solution and acetone was evaporated under reduced pressure. The residue was diluted with water and extracted with EtOAc. The combined organic layers were washed with NaCl solution and dried over Na2SO4. Filtration and concentration gave 8.94 g of an oily material, which was purified by column chromatography (SiO2 gel 50 g EtOAc in n-hexane 5–10%), to give 5.83 g (89.2%) of 5, as a pale yellow oil.

$^1$H-NMR δ(ppm, 500 MHz): 1.80 (1H, m), 1.93 (1H, m), 2.05 (1H, m), 2.14 (1H, m) 2.20–2.43 (3H), 3.63 (1H, dd, J=9.0 and 6.2 Hz), 3.67 (1H, dd, J=9.0 and 4.1 Hz), 4.49 (2H, s), 7.20–7.42 (5H).

(1R S, 2R S)-2-Benzyloxymethyl-1-methylcyclopentan-1-ol 6a and its (1S R, 2R S)-isomer 6b.

To a solution of 5 (5.83 g, 28.5 mmol) in diethyl ether (60 mL) methylmagnesium bromide (3.0M solution in diethyl ether; 10.5 mL, 31.5 mmol) was added dropwise over a period of 5 min under nitrogen in an ice bath. The mixture was stirred for 10 min and the reaction was quenched by an addition of NH4Cl solution. The organic layer was separated and the aqueous layer was extracted with diethyl ether. The combined organic layers were washed with NaCl solution, and dried over Na2SO4. Filtration and concentration gave 6.57 g of an oily material. Repeated chromatographic separation on SiO2 gel gave 3.11 g (49.5%) of 6a, as a pale yellow oil, and 2.18 g (34.7%) of 6b, as a colorless oil.

$^1$H-NMR δ(ppm, 500 MHz): 6a 1.34 (3H, s), 1.49–1.94 (7H), 2.78 (1H, br s), 3.65 (2H), 4.51 (1H, d, J=11.9 Hz), 4.56 (1H, d, J=11.9 Hz), 7.25–7.42 (5H); 6b 1.19 (3H, s), 1.48–1.88 (6H), 2.22 (1H, m), 2.57 (1H, br s), 3.45 (1H, t, J=8.8 Hz), 3.53 (1H, dd, J=8.8 and 4.6 Hz), 4.51 (2H, s), 7.26–7.45 (5H).

(1R S, 2R S)-2-Hydroxymethyl-1-methylcyclopentan-1-ol 7a.

A solution of 6a (3.11 g. 14.1 mmol) in ethanol (60 mL) was hydrogenated over palladium-charcoal (10%, 0.3 g) at ambient temperature for 1.5 h. The mixture was filtered through a pad of Celite. The filtrate was concentrated to give 1.78 g of 7a, which was used in the next reaction without further purification.

(1S R, 2R S)-2-Hydroxymethyl-1-methylcyclopentan-1-ol 7b.

In the same manner as for 7a, 6b (2.18 g, 9.90 mmol) was converted into 1.05 g of 7b, which was used in the next reaction without further purification.

(1R S, 2R S)-1-Methyl-2-p-toluenesulfonyloxymethylcyclopentan-1-ol 8a.

To a mixture of 7a (1.78 g, crude), pyridine (5.5 mL, 68.0 mmol) and 4-dimethylaminopyridine (0.17 g, 1.37 mmol) in CH$_2$Cl$_2$ (40 mL) was added p-toluenesulfonyl chloride (3.13 g, 16.4 mmol) in one portion, and the mixture was left to stand at 4° C. overnight. The mixture was stirred at ambient temperature for 100 min. To the mixture was added ice and the mixture was stirred at ambient temperature and the organic layer was separated. The aqueous layer was extracted with EtOAc and ,he combined organic layers were washed with water, CuSO$_4$ solution, water, NaHCO$_3$ solution and NaCl solution, and dried over Na$_2$SO$_4$. Filtration and concentration gave 3.86 g of 8a, which was used in the next reaction without further purification.

(1S R, 2R S)-1-Methyl-2-p-toluenesulfonyloxymethylcyclopentan-1-ol 8b.

In the same manner as for 8a, 7b (1.05 g, crude) was converted into 2.12 g of 8b, which was used in the next reaction without further purification.

(1R S, 2S R)-1-Methyl-2-phenylthiomethylcyclopentan-1-ol 9a.

To a solution of 8a (3.86 g, crude) and triethylamine (9.6 mL, 68.9 mmol) in N,N-dimethylformamide (30 mL) was added thiophenol (2.1 mL, 20.5 mL) in one portion, and the mixture was stirred at ambient temperature overnight. To the mixture was added thiophenol (1.1 mL) and the mixture was stirred for 40 min. To the mixture was added NaI (catalytic amount) and the mixture was stirred for 85 min. To the mixture was added triethylamine (5 mL) and the mixture was stirred for 145 min. To the mixture was added thiophenol (2 mL) and tetra-n-butylammonium iodide (catalytic amount) and the mixture was stirred for 35 min. The mixture was poured into cold diluted HCl, and extracted with diethyl ether. The combined organic layers were washed with cold diluted HCl, water, NaHCO$_3$ solution and NaCl solution, and dried over Na$_2$SO$_4$. Filtration and concentration gave 6.40 g of an oily material, which was purified by column chromatography (SiO$_2$ gel 100 g, EtOAc in n-hexane 1-20%), to give 1.84 g (60.4% from 6a) of 9a, as a pale yellow oil.

$^1$H-NMR δ(ppm, 500 MHz): 1.35 (3H, s), 1.49-1.67 (3H), 1.67-1.80 (2H), 1.82 (1H, m), 2.02 (1H, m), 2.89 (1H, dd, J=12.2 and 9.0 Hz), 3.21 (1H, dd, J=12.2 and 9.0 Hz), 7.16 (1H, t, J=7.3 Hz), 7.28 (2H, dd, J=7.8 and 7.3 Hz), 7.33 (2H, d, J=7.8 Hz).

(1S R, 2S R)-1-Methyl-2-phenylthiomethylcyclopentan-1-ol 9b.

In the same manner as for 9a, 8b (2.12 g, crude) was convened into 1.48 g (82.5% from 6b) of 9b, as a pale yellow oil.

$^1$H-NMR δ(ppm, 500 MHz): 1.24 (3H, s), 1.36 (1H, m), 1.58 (1H, m), 1.62-1.81 (3H), 1.93 (1H, br s), 1.96-2.12 (2H), 2.81 (1H, dd, J=12.5 and 4.9 Hz), 3.07 (1H, dd, J=12.5 and 6.5 Hz), 7.19 (1H, t, J=7.2 Hz), 7.29 (2H, dd, J=7.6 and 7.2 Hz), 7.35 (2H, d, J=7.6 Hz).

(1R S, 2S R)-2-Benzenesulfonylmethyl-1-methylcyclopentan-1-ol 10a.

To a mixture of 9a (1.84 g, 8.28 mmol) and NaHCO$_3$ (2.45 g, 29.2 mmol) in a mixture of CH$_2$Cl$_2$ (40mL) and water (17 mL) was added mCPBA (85%, 3.36 g, 16.5 mmol) in portionwise with stirring vigorously in an ice bath. The mixture was stirred for 15 min. To the mixture were added water (16 mL), NaHCO$_3$ (2.45 g) and mCPBA (1.68 g), and stirring was continued for 20 min. The excess amount of peracid was decomposed with Na$_2$S$_2$O$_3$ solution in the presence of a catalytic mount of KI. The organic layer was separated, and the aqueous layer was extracted with EtOAc. The combined organic layers were washed with NaCl solution, and dried over Na$_2$SO$_4$. Filtration and concentration gave 2.69 g of 10a, as white solids, which was used in the next reaction without further purification.

(1S R, 2S R)-2-Benzenesulfonylmethyl-1methylcylopentan-1 -ol 10b.

In the same manner as for 10a, 9b (1.48 g, 6.66 mmol) was converted into 2.14 g of 10b, as a pale yellow viscous oil, which was used in the next reaction without further purification.

(1R S, 2S R)-2-Benzenesulfonylmethyl-1-methyl-1-triethylsiloxycyclopentane 11a.

To a solution of 10a (2.69 g, crude) and imidazole (5.6 g, 82.3 mmol) in CH$_2$Cl$_2$ (50 mL) was added chlorotriethylsilane (1.7 mL, 10.1 mmol), and the mixture was stirred at ambient temperature overnight. To the mixture were added 2,6-lutidine (1.9 mL, 16.3 mmol) and triethylsilyl trifluoromethanesulfonate (1.9 mL, 8.40 mmol), and the mixture was stirred at ambient temperature for 35 min, then heated under reflux. Heating and stirring were continued with further addition of triethylsilyl trifluoromethanesulfonate (0.8 mL) overnight. Ice was added to the mixture, and the organic layer was separated. The aqueous layer was extracted with n-hexane, and the combined organic layers were washed with cold diluted HCl , water, NaHCO$_3$ solution and NaCl solution, and dried over Na$_2$SO$_4$. Filtration and concentration, followed by chromatographic purification (SiO$_2$ gel 50 g, EtOAc in n-hexane 5%), to give 3.21 g (quantitative yield from 9a) of 11a, as a colorless oil.

$^1$H-NMR δ(ppm, 500 MHz): 0.54 (6H, q, J=7.9 Hz), 0.90 (9H, t, J=7.9 Hz), 1.21 (3H, s), 144-1.63 (3H), 1.63-1.78 (2H), 1.81-1.96 (2H), 3.07 (1H, dd, J=14.7 and 9.9 Hz), 3.31 (1H, d, J=14.7 Hz), 7.56 (2H, dd, J=7.5 and 7.4 Hz), 7.64 (1H, t, J=7.4 Hz), 7.92 (2H, d, J=7.5 Hz).

(1S R, 2S R)-2-Benzenesulfonylmethyl-1-methyl-1-triethylsiloxycyclopentane 11b.

In the same manner as for 11a, 10b (2.14 g, crude) was converted into 3.21 g (quantitative yield from 9b) of 11b, as a colorless oil.

$^1$H-NMR δ(ppm, 500 MHz): 0.46 (6H, q, J=7.8 Hz), 0.84 (9H, t, J=7.8 Hz), 0.99 (3H, s), 1.27 (1H, m), 1.45-1.75 (4H), 1.96-2.15 (2H), 2.89 (1H, dd, J=13.1 and 12.0 Hz), 3.37 (1H, d, J=13.1 Hz), 7.56 (2H, dd, J=8.0 and 7.4 Hz), 7.64 (1H, t, J=7.4 Hz), 7.91 (2H, d, J=8.0 Hz).

(22E, 24R, 25R)- and (22E, 24S, 25S)-3β-tert-Butyldiphenyl-siloxy-1α-methoxycarbonyloxy-26,28-methylene-25-triethylsiloxy-ergosta-5,7,22-triene 13a.

To a solution of 11a (574 mg, 1.56 mmol) in THF (10 mL) was added a solution of LiNEt$_2$ (prepared from 0.54 mL of diethylamine and 3.1 mL of 1.6N n-butyllithium in n-hexane in 6.8 mL of THF; 3.4 mL) dropwise under nitrogen in a dry ice-MeOH bath over a period of 30 min. A solution of (20S)-3β-tert-butyldiphenylsiloxy-1α-methoxycarbonyloxy-20-methylpregna-5,7-dien-21-al 12 (1.00 g, 1.56 mmol) in THF (10 mL) was added to the mixture dropwise at the same temperature over a period of 25 min. The reaction was quenched by an addition of NH$_4$Cl solution. and the mixture was allowed to warm to ambient temperature. The organic layer was separated, and the aqueous layer was extracted with EtOAc. The combined organic layers were washed with NaCl solution, and dried over Na$_2$SO$_4$. Filtration and concentration gave 1.84 g of a crude product, which was used in the next reaction without further purification.

A mixture of the crude product (1.84 g), 4-dimethylaminopyridine (1.91 g) and acetic anhydride (0.74 mL) in CH$_2$Cl$_2$ (40 mL) was stirred at ambient temperature under nitrogen overnight. To the mixture was added ice, and the mixture was stirred at ambient temperature. The organic layer was separated, and the aqueous layer was extracted with EtOAc. The combined organic layers were washed with NaCl solution, and dried over Na$_2$SO$_4$. Filtration and concentration gave 2.45 g of a crude product, as a pale yellow oil, which was used in the next reaction without further purification.

To a solution of the crude product (2.45 g) in a mixture of THF (20 mL) and MeOH (20 mL) was added Na$_2$HPO$_4$ (6.6 g, 46.5 mmol), and the mixture was stirred at −40°−−50° C. under nitrogen. To the mixture was added Na-Hg (5%, 7.17 g, 15.6 mmol), and the mixture was stirred at the same temperature for 1.5 h. To the mixture was added Na$_2$HPO4 (13.2 g) and Na-Hg (14.4 g), and the mixture was stirred at the same temperature for 1 h and then at −30°−−40° C. for 1.25 h. The mixture was filtered through a pad of Celite and washed with EtOAc. The filtrate and washings were poured into NaCl solution, and the organic layer was separated. The aqueous layer was extracted with EtOAc, and the combined organic layers were washed with NaCl solution, and dried over Na$_2$SO$_4$. Filtration and concentration gave 3.21 g of a crude product, which was purified by column chromatography (SiO$_2$ gel 50 g, EtOAc in n-hexane 1–3%), to give 719 mg (54.1%) of 13a, as white foams.

$^1$H-NMR δ(ppm, 500 MHz): 0.55 (6H, q, J=7.9 Hz), 0.60 (3H, s), 0.93 (9H, t, J=7.9 Hz), 0.98 (3H, s), 0.96–1.04 (3H), 1.05 (9H, s), 1.20 (3H, s), 2.47 (2H, d, J=7.9 Hz), 3.64 (3H, s), 3.97 (1H, m), 4.63 (1H, br s), 5.11–5.26 (1H), 5.26–5.43 (2H), 5.53 (1H, d, J=5.6 Hz), 7.32–7.45 (6H), 7.64 (4H, d, J=8.1 Hz).

(22E, 24R, 25S)- and (22E, 24S, 25R)-3β-tert-Butyldiphenyl-siloxy-25-triethylsiloxy-1α-methoxycarbonyloxy-26,28-methyleneergosta-5,7,22-triene 13b.

In the same manner as for 13a, 11b (574 mg, 1.56 mmol) was converted into 569 mg (42.8%) of 13b, as white foams.

$^1$H-NMR δ(ppm, 500 MHz): 0.55 (6H, q, J=7.9 Hz), 0.59 (3H, s), 0.93 (9H, t, J=7.9 Hz), 0.98 (3H, s), 0.96–1.03 (3H). 1.05 (9H, s), 1.08, 1.09 (3H, two s), 2.47 (2H, d, J=7.9 Hz), 3.64 (3H, s), 3.96 (1H, m), 4.63 (1H, br s), 5.10–5.28 (2H), 5.31 (1H, br s), 5.53 (1H, d, J=5.4 Hz), 7.31–7.47 (6H), 7.64 (4H, d, J=7.1 Hz).

(22E, 24R, 25R)- and (22E, 24S, 25S)-1α-Methoxycarbonyloxy-26,28-methyleneergosta-5,7,22-triene-3β,25-diol 14a.

To a solution 13a (719 mg, 0.845 mmol) in THF (15 mL) was added a solution of tetra-n-butylammonium fluoride (1.0M in THF, 2.5 mL), and the mixture was stirred at ambient temperature for 1.5 h. A solution of tetra-n-butylammonium fluoride (1.0M in THF, 2.5 mL) was added twice to the mixture, and the mixture was stirred at ambient temperature overnight. The mixture was poured into cold NaHCO$_3$ solution, and the mixture was extracted with EtOAc. The combined organic layers were washed with NaCl solution, and dried over Na$_2$SO$_4$. Filtration and concentration gave 0.97 g of a crude product, which was purified by column chromatography (SiO$_2$ gel 30 g, EtOAc in n-hexane 20–50%), to give 373 mg (88.5%) of 14a, as white solids.

$^1$H-NMR δ(ppm, 500 MHz): 0.64 (3H, s), 1.01 (3H, s), 1.05, 1.06 (3H, two d, J=5.8 and 6.1 Hz), 1.25 (3H, s), 3.78 (3H, s), 4.01 (1H, m), 4.82 (1H, br s), 5.28–5.48 (3H), 5.66 (1H).

(22E, 24R, 25S)- and (22E, 24S, 25R)-1α-Methoxycarbonyloxy-26,28-methyleneergosta-5,7,22-triene-3β,25-diol 14b.

In the same manner as for 14a, 13b (569 mg 0.668 mmol) was converted into 300 mg (90.2%) of 14b, as white solids.

$^1$H-NMR δ(ppm, 500 MHz): 0.63 (3H, s), 1.01 (3H, s), 1.04, 1.05 (3H, two d, J=7.1 Hz), 1.13 (3H, s), 3.78 (3H, s), 3.99 (1H, m), 4.82 (1H, br s), 5.25–5.35 (2H), 5.36 (1H), 5.66 (1H).

(22E, 24R, 25R)- and (22E, 24S, 25S)-26,28-Methylene-9,10-secoergosta-5,7,10(19),22-tetraene-1α,3β,25-triol 15a and 15a'.

A solution of 14a (100 mg, 0.201 mmol) in a mixture of diethyl ether (100 mL) and benzene (20 mL) was irradiated with a medium pressure mercury lamp through a Vycor filter for 30 min in an ice bath with nitrogen bubbling through the reaction mixture. The mixture was concentrated under reduced pressure, and the residue was dissolved in benzene (20 mL) md the solution was left to stand under nitrogen at ambient temperature for 16 days. The mixture was concentrated under reduced pressure and the residue was treated with 1N LiOH solution (1 mL) in MeOH (9 mL) in an ice bath under nitrogen for 6.3 h. The mixture was poured into ice water, and extracted with EtOAc. The combined organic layers were washed with NaCl solution and dried over Na$_2$SO$_4$. Filtration and concentration, followed by chromatographic purification (SiO$_2$ gel 5 g, EtOAc in n-hexane 50–80%), gave 22.9 mg of a diastereomeric mixture of 15a and 15a. Preparative HPLC [Zorbax Pro-10 SIL (Mitsui-Toatsu), 20 mm φ×250 mm, 80% EtOAc in n-hexane] gave 7.1 mg (8.0%) of 15a, which was eluted faster, and 12.9 mg (14.6%) of 15a', which was eluted slower.

15a: UV (EtOH): λmax 262 nm, λmin 228 nm.

$^1$H-NMR δ(ppm, 270 MHz): 0.56 (3H, s), 1.05 (3H, d, J=6.7 Hz), 1.24 (3H, s), 4.23 (1H, m), 4.43 (1H, m), 5.00

(1H, br s), 5.32 (1H, br s), 5.28–5.50 (2H), 6.01 (1H, d, J=11.0 Hz), 6.38 (1H, d, J=11.0 Hz).

MS m/z: 440 (M+), 422 (base peak), 404, 386, 269, 251, 155, 135, 105, 93, 81.

15a': UV (EtOH): λmax 261 nm, λmin 227 nm.

$^1$H-NMR δ(ppm, 270 MHz): 0.56 (3H, s), 1.0.4 (3H, d, J=6.7 Hz), 1.24 (3H, s), 4.23 (1H, m), 4.43 (1H, m), 5.00 (1H, br s), 5.23–5.48 (2H), 5.35 (1H, br s), 6.01 (1H, d, J=11.0 Hz), 6.38 (1H, d, J=11.0 Hz).

MS m/z: 440 (M+), 422 (base peak), 404, 386, 269, 251, 155, 135, 105, 93, 81.

(22E, 24R, 25S)- and (22E, 24S, 25R)-26,28-Methylene-9,10-secoergosta-5,7,10 (19) 22-tetraene-1α,3β,25-triol 15b and 15b'.

A solution of 14b (100 mg, 0.201 mmol) in a mixture of diethyl ether (100 mL) and benzene (20 mL) was irradiated with a medium pressure mercury lamp through a Vycor filter for 30 min in an ice bath with nitrogen bubbling through the reaction mixture. The mixture was concentrated under reduced pressure, and the residue was dissolved in benzene (20 mL) and the solution was left to stand under nitrogen at ambient temperature for 16 days. The mixture was concentrated under reduced pressure and the residue was treated with 1N LiOH solution (1 mL) in MeOH (9 mL) in an ice bath under nitrogen for 6.3 h. The mixture was poured into ice water, and extracted with EtOAc. The combined organic layers were washed with NaCl solution and dried over Na$_2$SO$_4$. Filtration and concentration, followed by chromatographic purification (SiO$_2$ gel 5 g, EtOAc in n-hexane 50–80%), gave 21.3 mg of a diastereomeric mixture of 15b and 15b'. Preparative HPLC [Zorbax Pro-10 SIL (Mitsui-Toatsu), 50 mm φ×250 mm, 80% EtOAc in n-hexane] gave 6.3 mg (7.1%) of 15b, which was eluted faster, and 4.5 mg (5.1%) of 15b', which was eluted slower.

15 b: UV (EtOH): λmax 263 nm, λmin 228 nm.

$^1$H-NMR δ(ppm, 270 MHz): 0.56 (3H, s), 1.03 (3H, d, J=6.7 Hz), 1.13 (3H, s), 4.23 (1H, m), 4.43 (1H, m), 5.00 (1H, br s), 5.14–5.43 (2H), 5.32 (1H, br s), 6.01 (1H, d, j=11.0 Hz), 6.38 (1H, d, J=11.0 Hz).

MS m/z: 440 (M+), 422 (base peak, 404, 386. 269, 251, 155, 135, 105, 93, 81.

15b': UV (EtOH): λmax 264 nm,λmin 227 nm.

$^1$H-NMR δ(ppm, 270 MHz): 0.56 (3H, s), 1.03 (3H, d, J=6.7 Hz), 1.13 (3H, s), 4.23 (1H, m), 4.43 (1H, m), 5.00 (1H, br s), 5.10–5.42 (2H), 5.32 (1H, br s), 6.01 (1H, d, j=11.0 Hz), 6.38 (1H, d, J=11.0 Hz).

MS m/Z: 440 (M+), 422 (base peak), 404, 386, 269, 251, 155, 135, 105, 93, 81.

BIOLOGICAL ACTIVITY

EXAMPLE 2

Calcemic Activity

Weanling male rats obtained from the Holtzman Company were fed a low calcium (0.02%), 0.3% phosphorus, vitamin D-deficient diet for three weeks. After this time, the animals were severely hypocalcemic. They were then implanted with Alzet minipumps that delivered approximately 13 μL of solution per day which contained the indicated dose in Tables 1 and 2 dissolved in 5% ethanol, 95% propylene glycol. After 7 days the rats were killed and the duodena were used for determination of intestinal calcium transport by the everted intestinal sac technique (Martin & DeLuca, 1967) and serum calcium (bone calcium mobilization). The tests were made against the 1α,25-dihydroxyvitamin D$_3$ standard and are reported in Tables 1 and 2.

TABLE 1

INTESTINAL CALCIUM TRANSPORT AND BONE CALCIUM MOBILIZING ACTIVITIES OF 26,28-METHYLENE-1α, 25-DIHYDROXYVITAMIN D$_2$ COMPOUNDS

| GROUP | AMOUNT μgs/d/ 7 days | S/M (mean ± S.E.M.) | SERUM CALCIUM (mean ± S.E.M.) (mg/100 ml) |
|---|---|---|---|
| D Deficient | 0 | 3.72 ± 0.31 | 3.81 ± 0.09 |
| LT I (15 b) | 0.1 | 9.08 ± 0.40 | 6.12 ± 0.65 |
|  | 0.5 | 9.85 ± 0.78 | 8.50 ± 0.33 |
| LT II (15 b') | 0.1 | 8.42 ± 0.50 | 4.8 ± 0.22 |
|  | 0.5 | 8.82 ± 0.70 | 5.8 ± 0.09 |
| 1,25(OH)$_2$D$_3$ | 0.1 | 9.1 ± 0.23 | 5.91 ± 0.12 |

Stereoisomers of 26,28 Methylene 1α,25(OH)$_2$D$_3$:

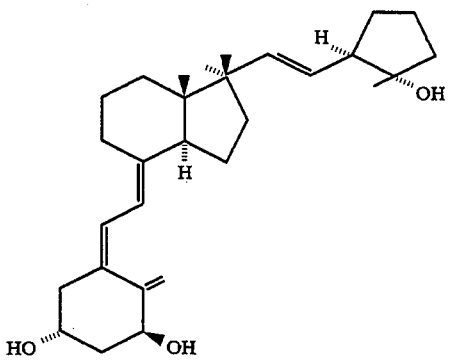

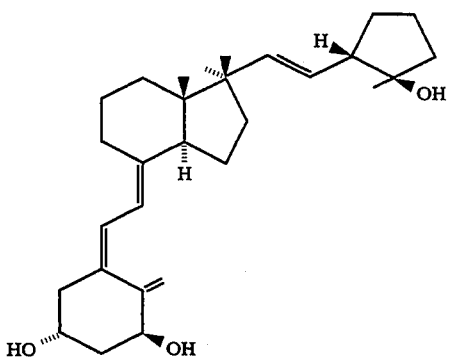

LT-isomers 15 b and 15 b'

The results show that the LT-II 26,28 methylene-1,25-dihydroxyvitamin D$_2$ compounds are less active than 1,25-dihydroxyvitamin D$_3$ in the mobilization of calcium from bone. The amount of bone calcium mobilizing activity is considerably less than 1,25-dihydroxyvitamin D$_3$. However, both of the 26,28-methylene-D$_2$ compounds have highly significant intestinal calcium transport activity. The LT compounds, therefore, by showing preferential activity on intestinal calcium transport and reduced calcium mobilizing activity in bone suggest that they would be preferred agents for the treatment of a disease where bone loss is a major issue, such as osteoporosis, osteomalacia and renal osteodystrophy. The LT-1 and UC compounds are effective on bone calcium mobilization and, therefore, would be useful where low bone turnover osteoporosis is found, i.e. age-related osteoporosis.

TABLE 2

| GROUP | AMOUNT µgs/d/ 7 days | S/M (mean ± S.E.M.) | SERUM CALCIUM (mean ± S.E.M.) (mg/100 ml) |
|---|---|---|---|
| D Deficient | 0 | 4.9 ± 0.16 | 4.6 ± 0.15 |
| UC I (15 a) | 0.1 | 8.6 ± 0.73 | 7.01 ± 0.21 |
|  | 0.5 | 6.2 ± 1.03 | 9.39 ± 0.18 |
| UC II (15 a') | 0.1 | 4.7 ± 0.39 | 6.15 ± 0.13 |
|  | 0.5 | 8.9 ± 1.07 | 9.48 ± 0.12 |
| 1,25(OH)$_2$D$_3$ | 0.1 | 9.0 ± 0.73 | 7.38 ± 0.61 |

Stereoisomers of 26,28 Methylene 1α,25(OH)$_2$D$_3$:

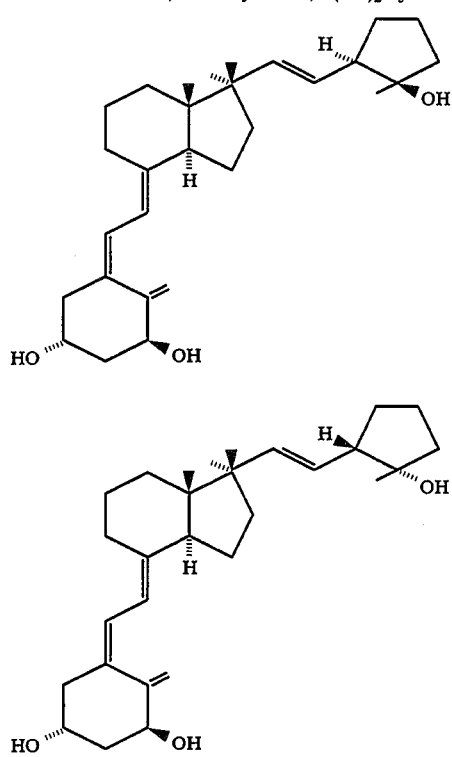

UC-isomers 15 a and 15 a'

For treatment purposes, the novel compounds of this invention may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds may be administered orally, parenterally or transdermally. The compounds are advantageously administered by injection or by intravenous infusion of suitable sterile solutions, or in the form of liquid or solid doses via the alimentary canal, or in the form of creams, ointments, patches, or similar vehicles suitable for transdermal applications. Doses of from 0.5 µg to 50 µg per day of the compounds are appropriate for treatment purposes, such doses being adjusted according to the disease to be treated, its severity and the response of the subject as is well understood in the art. Since the new compounds exhibit specificity of action, each may be suitably administered alone, in situations where only calcium transport stimulation is desired, or together with graded doses of another active vitamin D compound—e.g. 1α-hydroxyvitamin D$_2$ or D$_3$, or 1α,25-dihydroxyvitamin D$_3$—in situations where some degree of bone mineral mobilization (together with calcium transport stimulation) is found to be advantageous.

Process Scheme

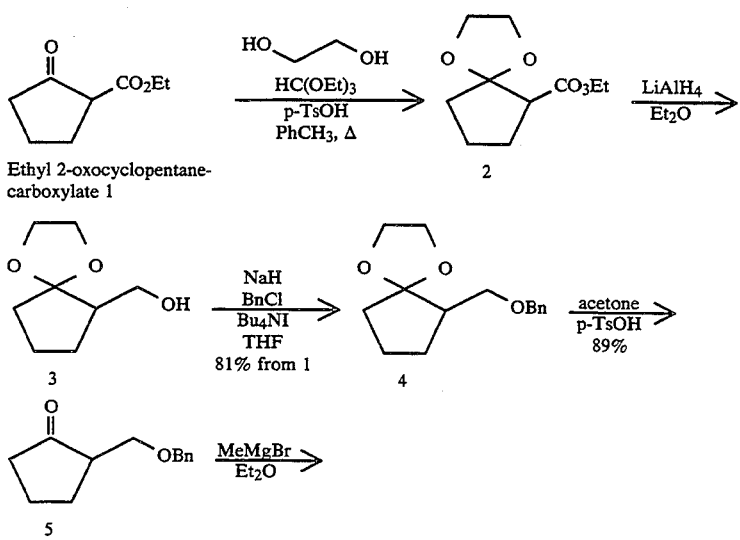

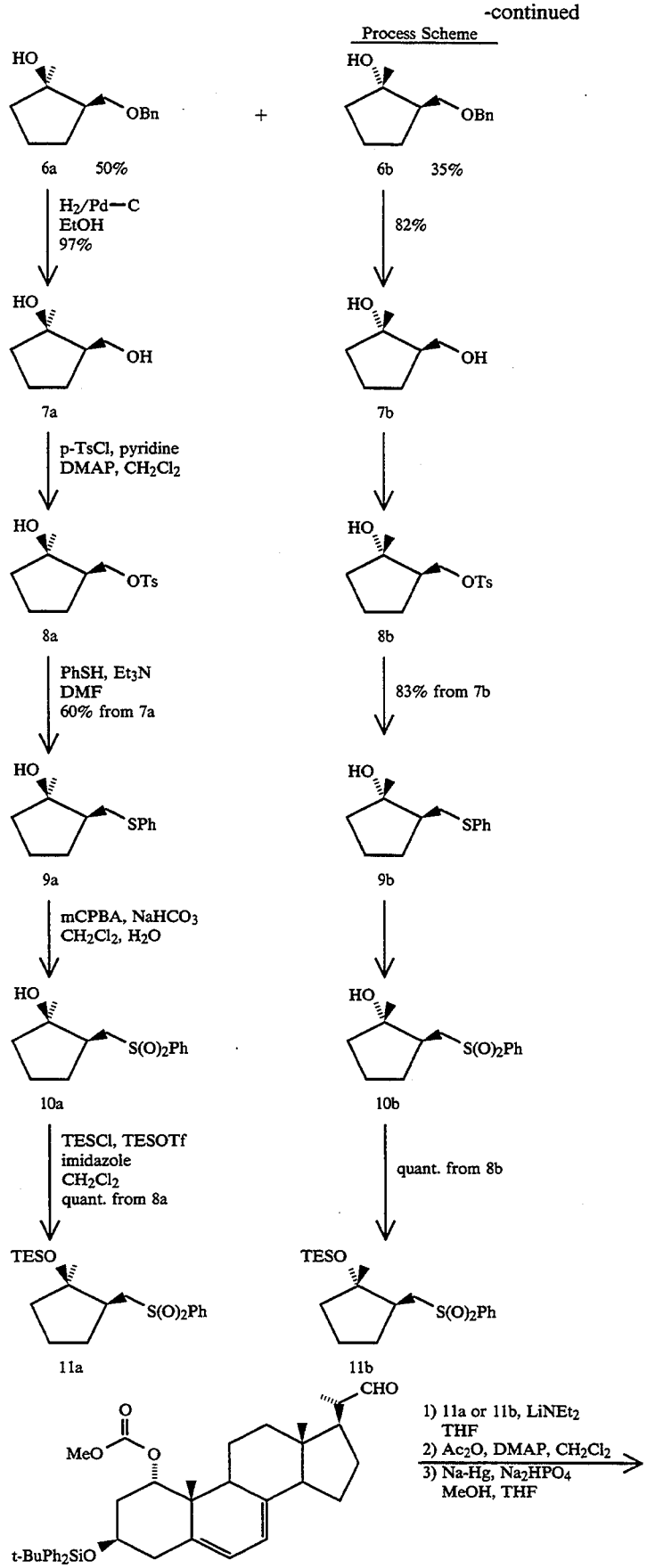

-continued
Process Scheme
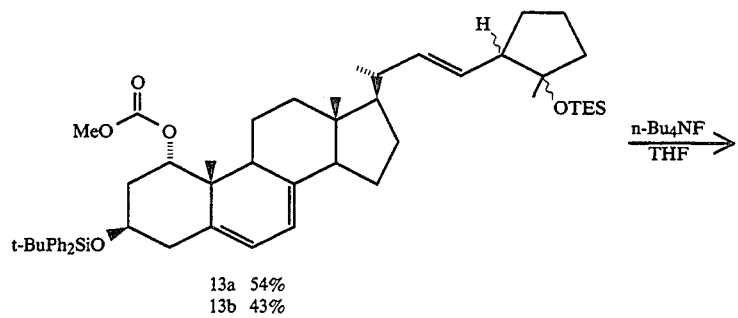
13a 54%
13b 43%
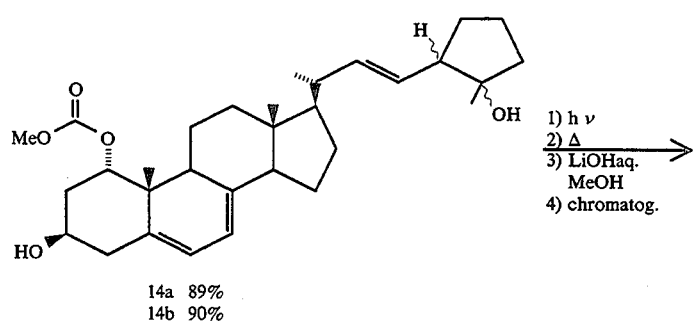
14a 89%
14b 90%
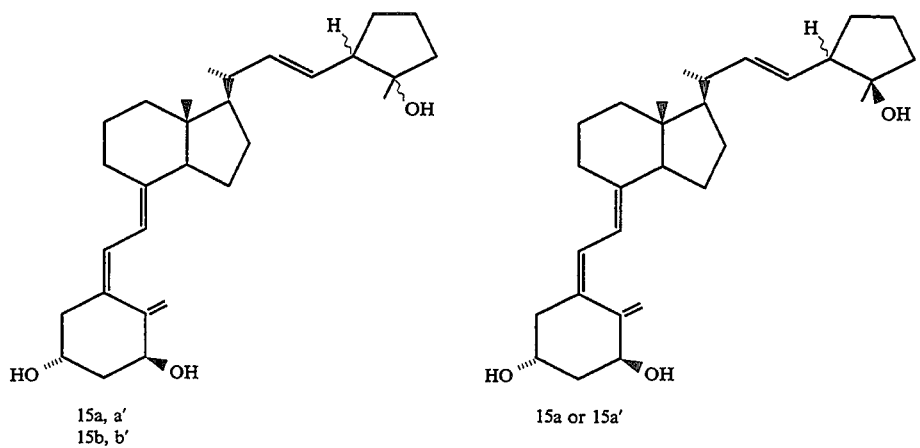
15a, a'
15b, b'
15a or 15a'
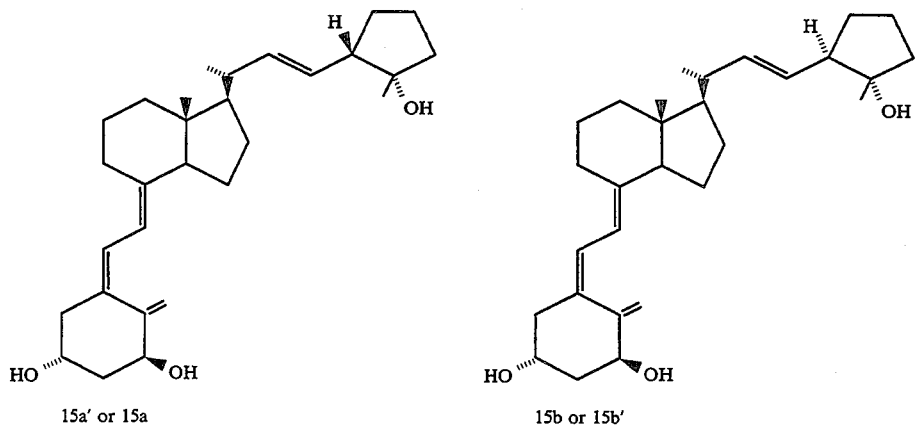
15a' or 15a
15b or 15b'

-continued
Process Scheme

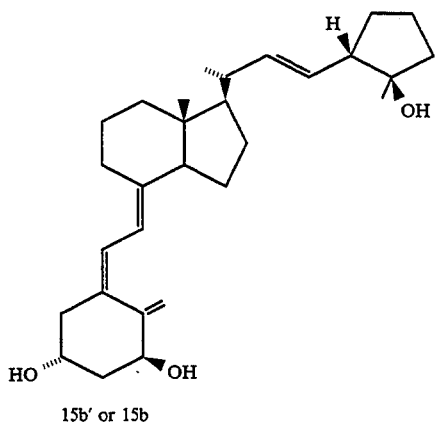

15b' or 15b

Various modes of carrying out the invention are contemplated as being within the scope of the following claims particularly pointing out and distinctly claiming the subject matter regarded as the invention.

We claim:

1. A compound having the formula

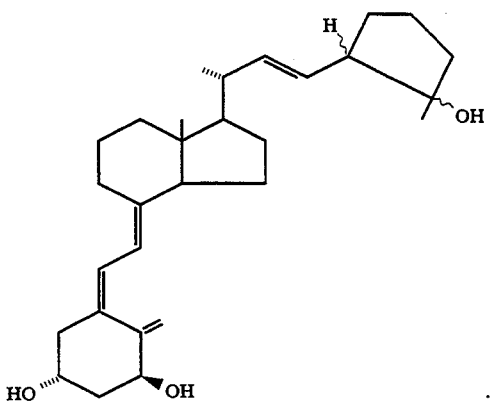

2. A pharmaceutical composition containing at least one compound as claimed in claim 1 together with a pharmaceutically acceptable excipient.

3. The pharmaceutical composition of claim 2 containing (22E, 24R, 25R)-26,28-methylene-1α,25-dihydroxyvitamin $D_2$ in an amount from about 0.5 μg to about 50 μg.

4. The pharmaceutical composition of claim 2 containing (22E, 24S, 25S)-26,28-methylene-1α,25-dihydroxyvitamin $D_2$ in an amount from about 0.5 μg to about 50 μg.

5. The pharmaceutical composition of claim 2 containing (22E, 24R, 25S)-26,28-methylene-1α,25-dihydroxyvitamin $D_2$ in an amount from about 0.5μg to about 50 μg.

6. The pharmaceutical composition of claim 2 containing (22E, 24S, 25R)-26,28-methylene-1α,25-dihydroxyvitamin $D_2$ in an amount from about 0.5 μg to about 50 μg.

7. (22E, 24R, 25R)-26,28-methylene-1α,25-dihydroxyvitamin $D_2$.

8. (22E, 24S, 25S)-26,28-methylene-1α,25-dihydroxyvitamin $D_2$.

9. (22E, 24R, 25S)-26,28-methylene-1α,25-dihydroxyvitamin $D_2$.

10. (22E, 24S, 25R)-26,28-methylene-1α,25-dihydroxyvitamin $D_2$.

11. A method of treating metabolic bone disease where it is desired to maintain or increase bone mass comprising administering to a patient with said disease a compound having the formula

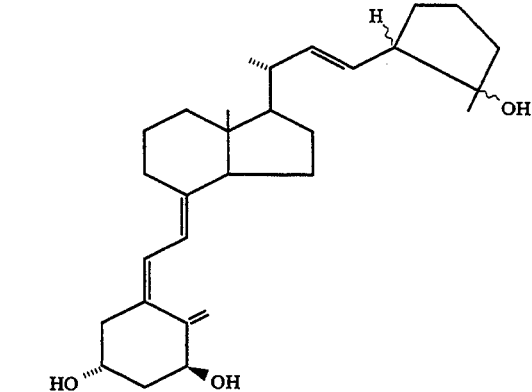

12. The method of claim 11 where the disease is osteoporosis.

13. The method of claim 11 where the disease is osteomalacia.

14. The method of claim 11 where the disease is renal osteodystrophy.

15. The method of claim 11 where the compound is administered orally.

16. The method of claim 11 where the compound is administered parenterally.

17. The method of claim 11 where the compound is administered transdermally.

18. The method of claim 11 where the compound is administered in a dosage of from 0.5 μg to 50 μg per day.

* * * * *